(12) United States Patent
Martin-Hill

(10) Patent No.: US 9,820,880 B1
(45) Date of Patent: Nov. 21, 2017

(54) URINARY BAG COLLECTION COVER

(71) Applicant: Glenda Martin-Hill, Riverview, FL (US)

(72) Inventor: Glenda Martin-Hill, Riverview, FL (US)

( * ) Notice: Subject to any disclaimer, the term of this patent is extended or adjusted under 35 U.S.C. 154(b) by 163 days.

(21) Appl. No.: 14/936,995

(22) Filed: Nov. 10, 2015

(51) Int. Cl.
*A61B 17/06* (2006.01)
*A61B 19/02* (2006.01)
*A61L 15/00* (2006.01)
*A61F 5/44* (2006.01)
*A61F 5/441* (2006.01)

(52) U.S. Cl.
CPC ............ *A61F 5/4404* (2013.01); *A61F 5/441* (2013.01)

(58) Field of Classification Search
CPC ........ A61F 5/4404; A61F 5/441; A61B 17/06; A61B 19/02; A61L 15/00
USPC ........ 206/438, 210, 363, 439; 604/317, 349, 604/318, 319
See application file for complete search history.

(56) References Cited

U.S. PATENT DOCUMENTS

| | | | |
|---|---|---|---|
| 2,800,905 A * | 7/1957 | Simmons | A61M 3/0245 128/DIG. 24 |
| 4,331,148 A | 5/1982 | Steer | |
| 4,874,387 A | 10/1989 | Boone | |
| D316,602 S | 4/1991 | Dungan et al. | |
| 6,165,159 A * | 12/2000 | Blanton | A61F 5/441 604/333 |
| 6,406,463 B1 * | 6/2002 | Brown | A61G 9/006 4/144.1 |
| 7,691,091 B1 | 4/2010 | Baggett | |
| D618,340 S | 6/2010 | Marshall | |
| 8,348,914 B2 | 1/2013 | Zyburt | |
| 2002/0077609 A1 | 6/2002 | Johnson | |
| 2009/0234310 A1 | 9/2009 | Marshall | |
| 2009/0270822 A1 * | 10/2009 | Medeiros | A61F 5/453 604/347 |
| 2012/0082403 A1 * | 4/2012 | Zyburt | A61F 5/445 383/42 |
| 2014/0257215 A1 * | 9/2014 | Timms | A61F 5/441 604/333 |

* cited by examiner

Primary Examiner — J. Gregory Pickett
Assistant Examiner — Rafael Ortiz

(57) ABSTRACT

The urinary bag collection cover is designed to hold and conceal the sight and smell of the drainage bag for a Foley catheter. The urinary bag collection cover is a bag featuring a drawstring closure and handle on the top of the bag that allows the bag to be hung from a hook. The urinary bag collection cover is lined with a polyethylene liner. The bottom of the urinary bag collection cover is fitted with a container within which a deodorizer is placed to mask the potential smell of urine. A port is provided in the urinary bag collection cover to allow for the insertion of a drainage tube to draw off the urine collected in the urinary bag collection. The urinary bag collection cover comprises a bag, a handle, a drawstring, a drainage port, and a deodorizer container.

5 Claims, 5 Drawing Sheets

URINARY BAG COLLECTION COVER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of protective covers for body entering conduits, more specifically, a cover adapted for use with a collection bag for a Foley catheter.

SUMMARY OF INVENTION

The urinary bag collection cover is designed to hold and conceal the sight and smell of the drainage bag for a Foley catheter. The urinary bag collection cover is a bag featuring a drawstring closure and handle on the top of the bag that allows the bag to be hung from a hook. The urinary bag collection cover is lined with a polyethylene liner. The bottom of the urinary bag collection cover is fitted with a container within which a deodorizer is placed to mask the potential smell of urine. A port is provided in the urinary bag collection cover to allow for the insertion of a drainage tube to draw off the urine collected in the urinary bag collection.

These together with additional objects, features and advantages of the urinary bag collection cover will be readily apparent to those of ordinary skill in the art upon reading the following detailed description of the presently preferred, but nonetheless illustrative, embodiments when taken in conjunction with the accompanying drawings.

In this respect, before explaining the current embodiments of the urinary bag collection cover in detail, it is to be understood that the urinary bag collection cover is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the urinary bag collection cover.

It is therefore important that the claims be regarded as including such equivalent construction insofar as they do not depart from the spirit and scope of the urinary bag collection cover. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
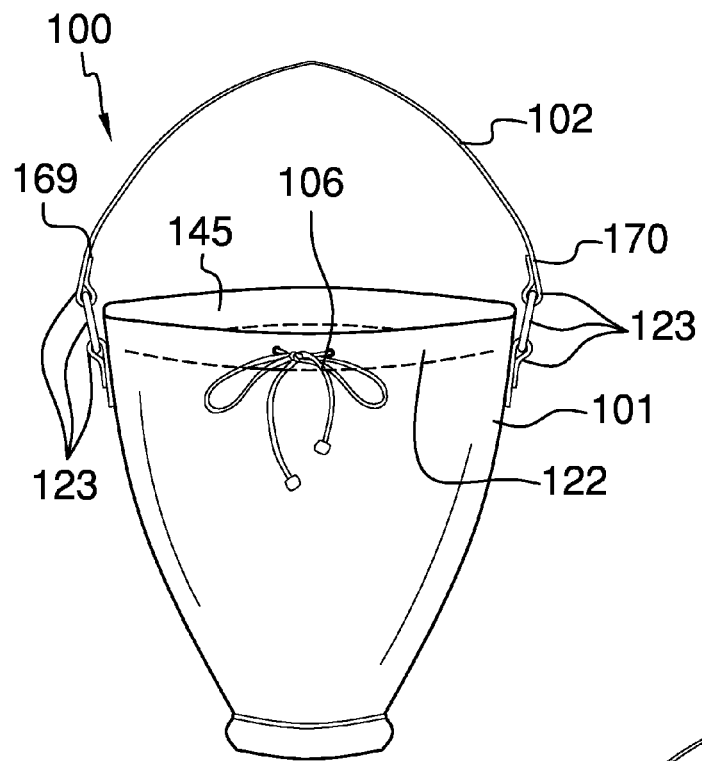
FIG. 1 is a front view of an embodiment of the disclosure.
Figure 2:
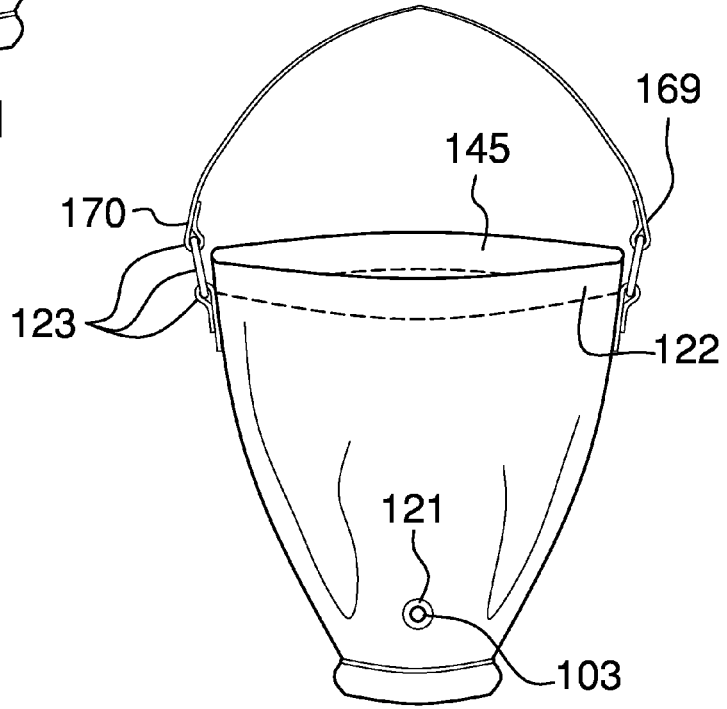
FIG. 2 is a back view of an embodiment of the disclosure.
Figure 4:
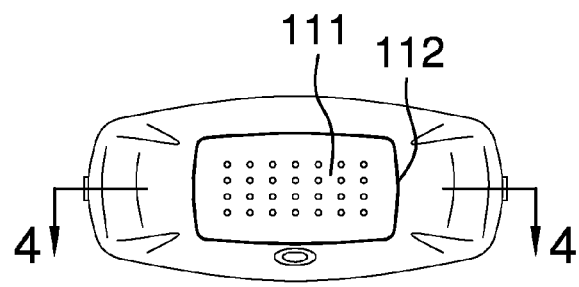
FIG. 4 is a bottom view of an embodiment of the disclosure.
Figure 3:
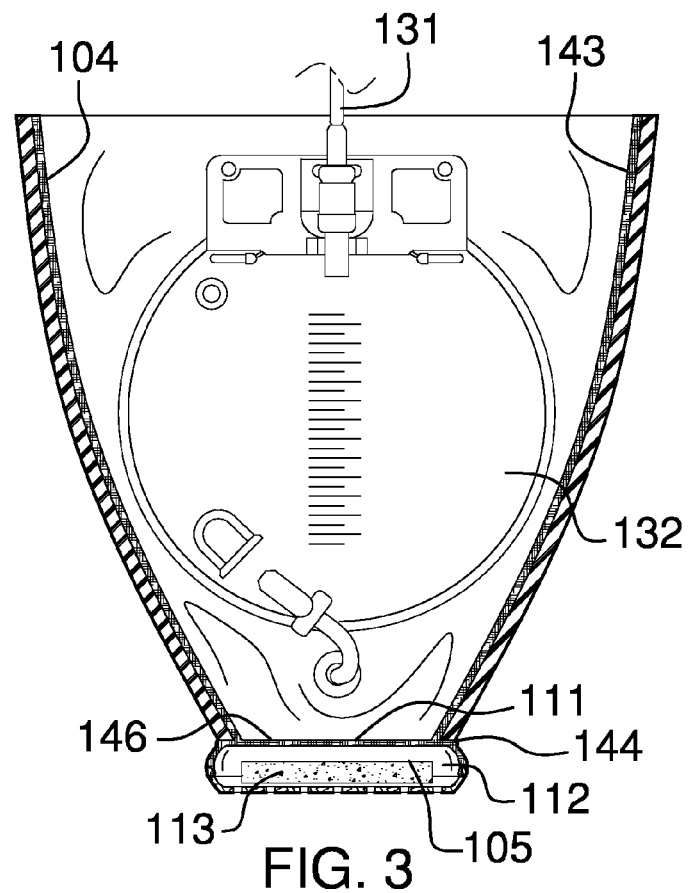
FIG. 3 is a cross-sectional view of an embodiment of the disclosure across 3-3.
Figure 5:
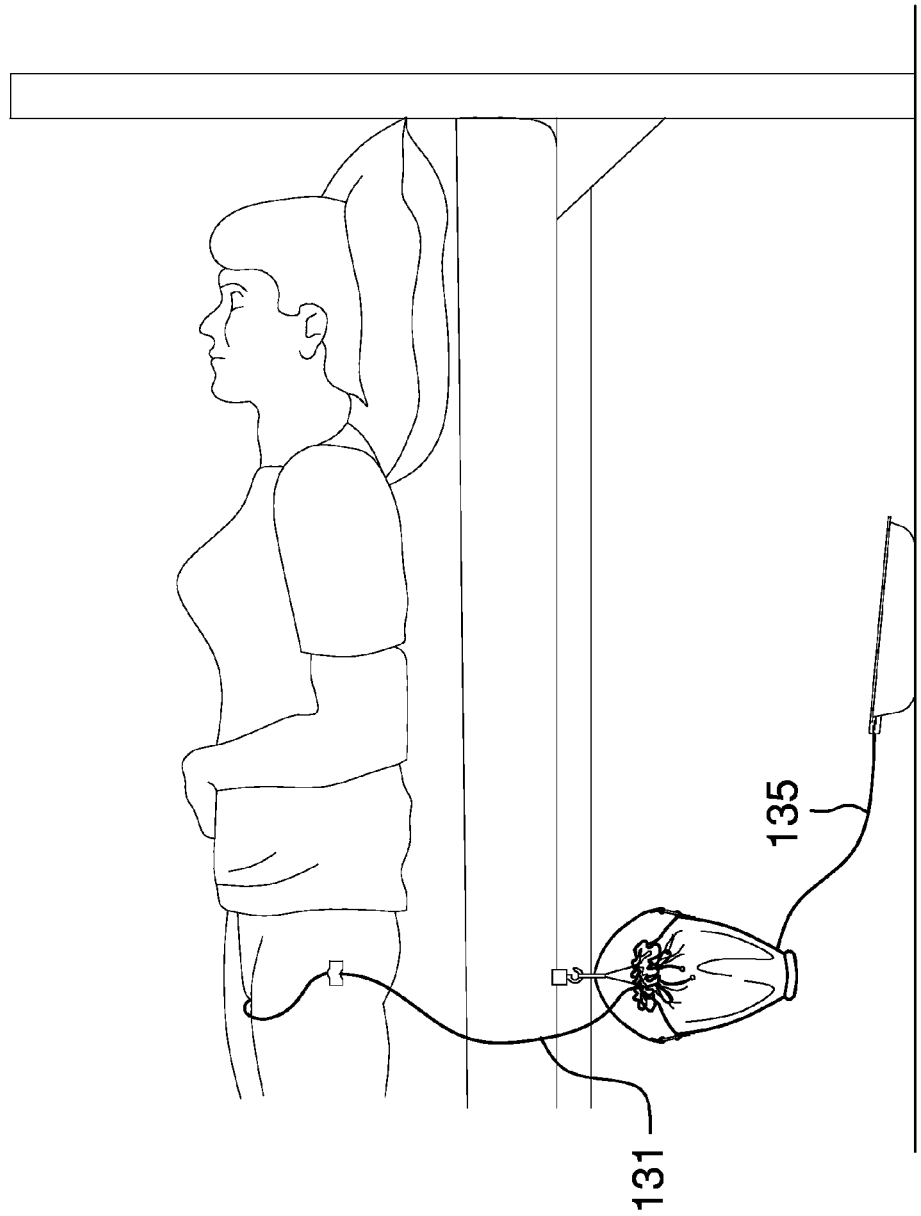
FIG. 5 is an in use view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 7. The urinary bag collection cover 100 (hereinafter invention) comprises a bag 101, a handle 102, a drawstring 106, a drainage port 103, and a deodorizer container 105.

Figure 6:
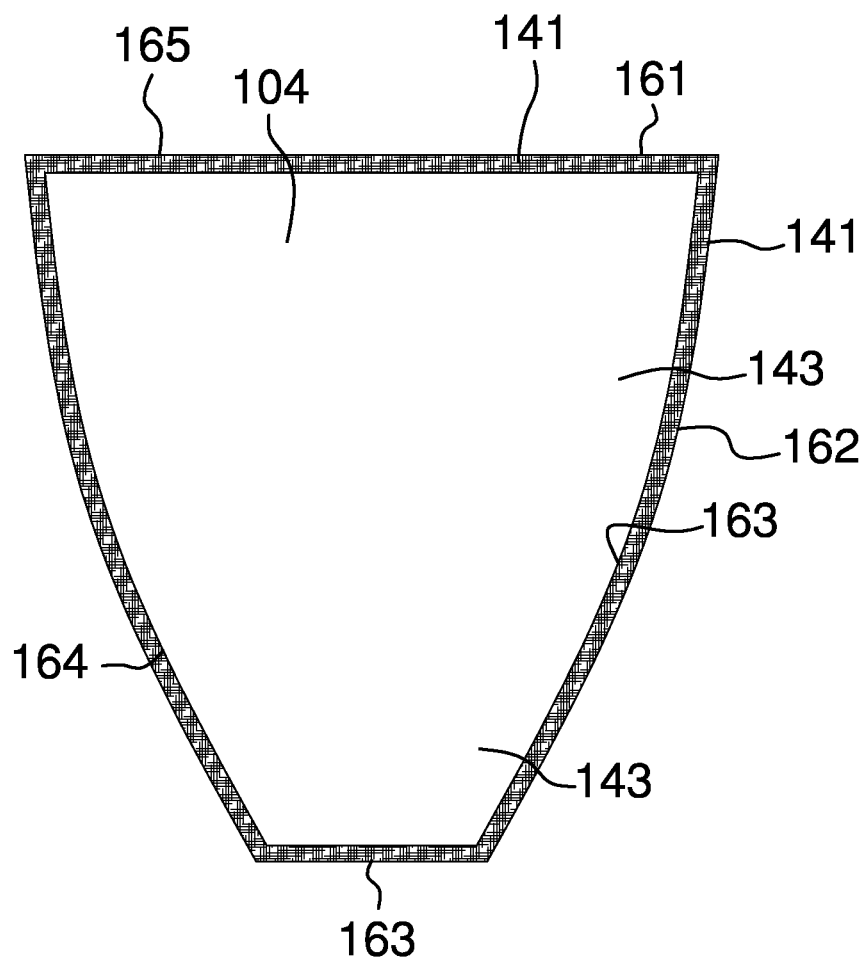
FIG. 6 is a detail view of an embodiment of the disclosure.

The bag 101 is the actual container that is used to hold the urinary collection bag 132 associated with a Foley catheter 131. The bag 101 further comprises a first textile 141, a second textile 142 and a liner 104. The liner 104 further comprises a first liner 143 and a second liner 144. As shown in FIG. 6, the first textile 141 is a textile material is cut in the shape of a trapezoid. The first perimeter 165 of the first textile 141 is further defined with a first side 161, a second side 162, a third side 163 and a fourth side 164. The first liner 143 is a sheeting material cut in the shape of a trapezoid such that the third perimeter 167 of the first liner 143 fits within the first perimeter 165 of the first textile 141. The first liner 143 is attached to the first textile 141 through the use of sewn seams or glue. The second textile 142 is a textile material that is cut in the form of an ellipse 133. The second liner 144 is a sheeting material that is cut in the shape of an ellipse 133. The second textile 142 is further defined with a second perimeter 166.

Figure 7:
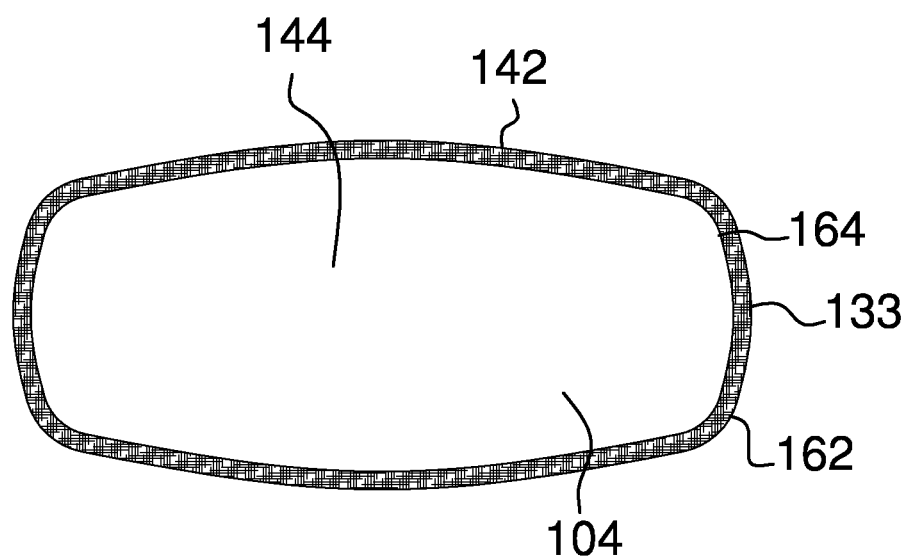
FIG. 7 is a detail view of an embodiment of the disclosure.

As shown in FIG. 7, the fourth perimeter 168 of the second liner 144 is less than the second perimeter 166 of the second textile 142 such that the second liner 144 will fit within the second perimeter 166 of the second textile 142. The second liner 144 is attached to the second textile 142 through the use of sewn seams or glue.

To assemble the bag 101, the second side 162 of the first textile 141 is folded around to join the fourth side 164 of the first textile 141 such that the liner 104 is on the interior surface of the resulting cone. The second side 162 and the first textile 141 is sewn to the fourth side 164 of the first textile 141. When the second side 162 and the fourth side 164 are sewn together, the first textile 141 further comprises a first opening 145 formed by the first side 161 and a second opening 146 formed by the third side 163. The dimensions of the first textile 141 are selected such that the urinary collection bag 132 associated with the Foley catheter 131 will readily fit into the bag 101. The dimensions of the first textile 141 are also selected such that the third side 163 of the first textile can be sewn to the second perimeter 166 of the second textile 142 thereby closing the second opening 146.

The first textile 141 and the second textile 142 are made of the same material. Suitable materials for the first textile 141 and the second textile 142 include, but are not limited to, fabric or a plastic sheeting. A plastic sheeting designed to simulate leather is preferred. The first liner 143 and the second liner 144 are formed from plastic sheeting. Suitable materials for the first liner 143 and the second liner 144 includes, but is not limited to, polyethylene.

The deodorizer container 105 is an enclosed object, such as a box 112, that is used to hold a deodorizing material. The deodorizer container 105 is made of a waterproof material and is formed such that the deodorizer container 105 will fit on top of the second textile 142 after it has been sewn to the third end of the first textile 141. A deodorizer 113 is placed inside the deodorizer container 105. While any deodorizer is appropriate, a bamboo charcoal deodorizer is preferred. The deodorizer container 105 further comprises a plurality of vents 111 to allow air to flow into and out of the deodorizer container 105 so that the deodorizer 113 will work. The deodorizer container 105 can be glued to the second liner 144.

A drainage port 103 is a hole formed into the first textile 141 and the first liner 143 of the bag 101. The purpose of the drainage port 103 is to allow the insertion of a drainage tube 135 that allows the urine collected in the urinary collection bag 132 to be drained to its final destination. The drainage port 103 is reinforced with a drainage port grommet 121.

The first opening 145 of the bag 101 is fitted with a drawstring 106. The drawstring 106 is a cord that is used to close the first opening 145. The drawstring 106 can be a simple cord that is wrapped around the first opening 145, or, alternatively, a channel 122 can be formed within which the drawstring 106 can be placed. The construction use of drawstrings 106 to close bags is well known and documented in the art.

The handle 102 is a strap. It is preferred that the strap is made of the same material as the first textile 141 and the second textile 142. The handle 102 is further defined with a first end 169 and a second end 170. The first end 169 and the second end 170 can be attached to the first textile 141 of the bag 101 using a sewn seam, glue, or hardware 123. In the first potential embodiment of the disclosure, commercially available hardware was used to attach the handle 102 to the bag 101.

To use the invention 100, a deodorizer 113 is placed inside the deodorizer container 105. The Foley catheter 131 is inserted into the urinary collection bag 132. The urinary collection bag 132 is inserted into the bag 101 through the first opening 145. A drainage tube 135 is inserted through the drainage port 103 and is attached to the urinary collection bag 132. The drawstring 106 is used to close the first opening 145 around the Foley catheter 131 in such a way that the drawstring 106 does not interfere with the flow of urine through the Foley catheter 131. The invention 100 is then hung from a hook by the handle 102 for storage.

The following definitions were used in this disclosure:

Cord: As used in this definition, a cord is a long, thin, and flexible piece of string, line, or rope. Cords are made from yarns, piles, or strands of material that are braided or twisted together. Cords have tensile strength but are too flexible to provide compressive strength and are not suitable for use in pushing objects. String, line, and rope are synonyms for cord.

Grommet: As used in this disclosure, a grommet is an eyelet placed in a hole in a textile, sheet, or panel that protects a rope hook or cable passed through it and to protect the textile, sheet, or panel from being torn.

Perimeter: As used in this disclosure, a perimeter is one or more curved or straight lines that bounds an enclosed area on a plane.

Sheeting: As used in this disclosure, sheeting is a material, such as cloth or plastic, in the form of a thin flexible layer or layers that is used to cover something.

Strap: As used in this disclosure, a strap is a strip of a flexible material that is used to fasten, secure, or carry an object.

Textile: As used in this disclosure, a textile is a material that is woven, knitted, or felted. Synonyms in common usage for this definition include fabric and cloth.

With respect to the above description, it is to be realized that the optimum dimensional relationship for the various components of the invention described above and in FIGS. 1 through 7, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A container comprising:
   a bag, a handle, a drawstring, a drainage port, and a deodorizer container;
   wherein the container is adapted for use with a urinary collection bag associated with a Foley catheter;
   wherein the container conceals the urinary collection bag associated with a Foley catheter from view;
   wherein the container masks the smell associated with the urinary collection bag associated with a Foley catheter;
   wherein the bag further comprises a first textile, a second textile and a liner;
   wherein the liner further comprises a first liner and a second liner;
   wherein the first textile is a textile material is cut in the shape of a trapezoid;
   wherein the first textile is further defined with a first perimeter;
   wherein the first perimeter is further defined with a first side, a second side, a third side and a fourth side;
   wherein the first liner is a sheeting material cut in the shape of a trapezoid;
   wherein the first liner is further defined with a third perimeter;

wherein the third perimeter fits within the boundaries defined by the first perimeter;

wherein the first liner is attached to the first textile;

wherein the second textile is a textile material that is cut in the form of an ellipse;

wherein the second textile is further defined with a second perimeter;

wherein the second liner is a sheeting material that is cut in the shape of an ellipse;

wherein the second liner is further defined with a fourth perimeter;

wherein the fourth perimeter fits within the boundaries defined by the second perimeter;

wherein the fourth liner is attached to the second textile;

wherein the second side of the first textile is attached to the fourth side of the first textile such that the liner is on the interior surface of the resulting cone;

wherein the first textile further comprises a first opening formed by the first side and a second opening formed by the third side;

wherein the second side of the first textile is attached to the fourth side of the first textile;

wherein the dimensions of the first textile are selected such that the urinary collection bag associated with the Foley catheter will fit into the bag;

wherein the dimensions of the first textile are selected such that the third side of the first textile can be sewn to the second perimeter;

wherein the deodorizer container is an enclosed object that further comprises a plurality of vents;

wherein the deodorizer container fits below the second liner.

2. The container according to claim 1 wherein a deodorizer is placed inside the deodorizer container.

3. The container according to claim 2 wherein the drainage port is a hole formed into the first textile and the first liner of the bag.

4. The container according to claim 3 wherein the first opening of the bag is fitted with a drawstring.

5. The container according to claim 4 wherein the handle is a strap;

wherein the handle is further defined with a first end and a second end;

wherein the first end and the second end are attached to the first textile.

* * * * *